United States Patent
O'Donnell

Patent Number: 5,554,149
Date of Patent: Sep. 10, 1996

[54] MALE INCONTINENCE PANTS

[76] Inventor: Doris O'Donnell, P.O. Box 363, Lincoln Park, N.J. 07035

[21] Appl. No.: 490,234

[22] Filed: Jun. 14, 1995

[51] Int. Cl.⁶ ................................................. A61F 13/15
[52] U.S. Cl. ........................................ 604/385.1; 604/349
[58] Field of Search ................................. 604/349–353, 604/358, 385.1

[56] References Cited

U.S. PATENT DOCUMENTS

| | | | |
|---|---|---|---|
| 2,445,220 | 7/1948 | Isaacson | 604/349 |
| 4,710,187 | 12/1987 | Boland et al. | 604/385.1 |
| 5,399,176 | 3/1995 | Chen | 604/349 |
| 5,429,622 | 7/1995 | Chung | 604/385.1 |

FOREIGN PATENT DOCUMENTS 8601710  3/1986  WIPO ................................. 604/317

Primary Examiner—Robert A. H. Clarke

[57] ABSTRACT

The male incontinence pants structure includes a single, flexible web having first and second web members with a connecting web extending therebetween, and interposed between the first and second web members are key-hole shaped openings to accommodate the legs and provide for linear seam engagement between the first and second webs employing such fasteners as tape members. A pocket member is integral with the second web, such that a slot member is arranged to accommodate the penile and scrotum portions of a male anatomy within the bag structure to accommodate involuntary discharge within the bag structure.

3 Claims, 3 Drawing Sheets

MALE INCONTINENCE PANTS

TECHNICAL FIELD

The field of invention is directed to pants-like structure for the containment of bodily fluid relative to male incontinence, and more specifically to a pants-like structure of enhanced efficiency and comfort in use.

BACKGROUND OF THE INVENTION

Prior art male incontinence pants-like structure have been presented in the prior art and indicated in the U.S. Pat. Nos. 4,589,877; 4,944,733; 5,009,649; 5,074,853; 5,267,989; U.S. Pat. Nos. Design D316,149; and D320,854.

SUMMARY OF THE INVENTION

The male incontinence pants structure includes a single, flexible web having first and second web members with a connecting web extending therebetween, and interposed between the first and second web members are key-hole shaped openings to accommodate the legs and provide for linear seam engagement between the first and second webs employing such fasteners as tape members. A pocket member is integral with the second web, such that a slot member is arranged to accommodate the penile and scrotum portions of a male anatomy within the bag structure to accommodate involuntary discharge within the bag structure.

Objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DESCRIPTION OF THE PREFERRED EMBODIMENT

As required, detailed embodiments of the present invention are disclosed herein; however, it is to be understood that the disclosed embodiments are merely exemplary of the invention, which may be embodied in various forms. Therefore specific structural and functional details disclosed herein are not to be interpreted as limiting, but merely as a basis for the claims and as a representative basis for teaching one skilled in the art to variously employ the present invention in virtually any appropriately detailed structure.

Figure 3:
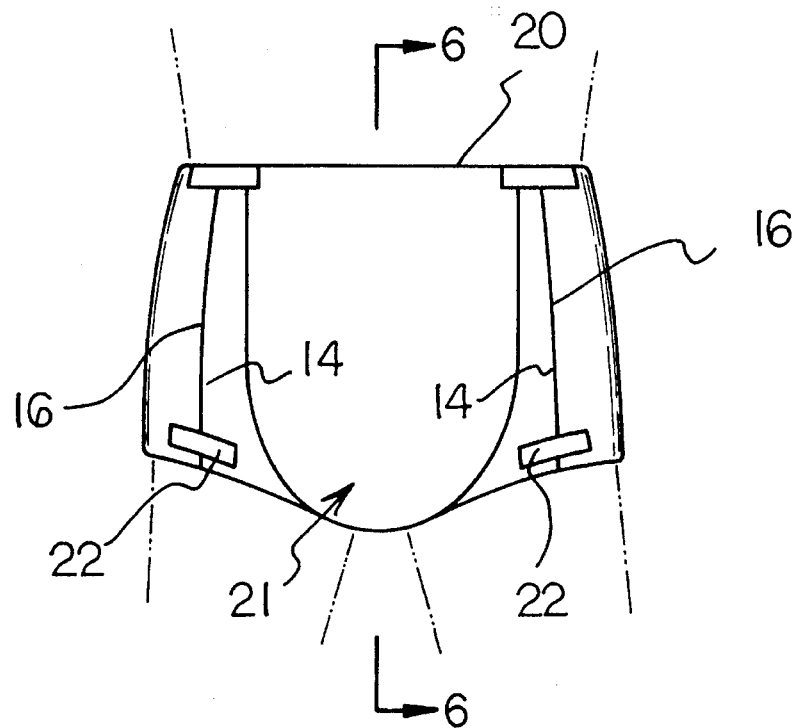
FIG. 3 is a front view, taken in elevation, of the pants construction as worn by an individual.
Figure 4:
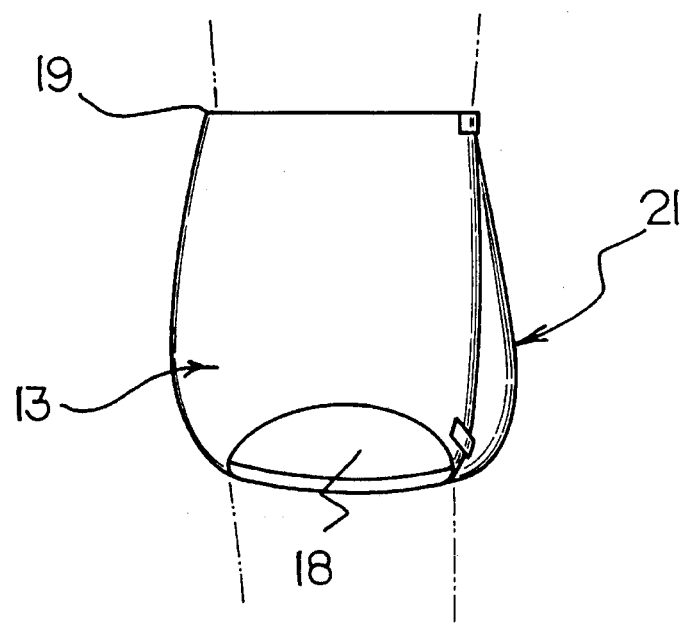
FIG. 4 is a side view, taken in elevation, of the pants structure as worn by an individual.
Figure 5:
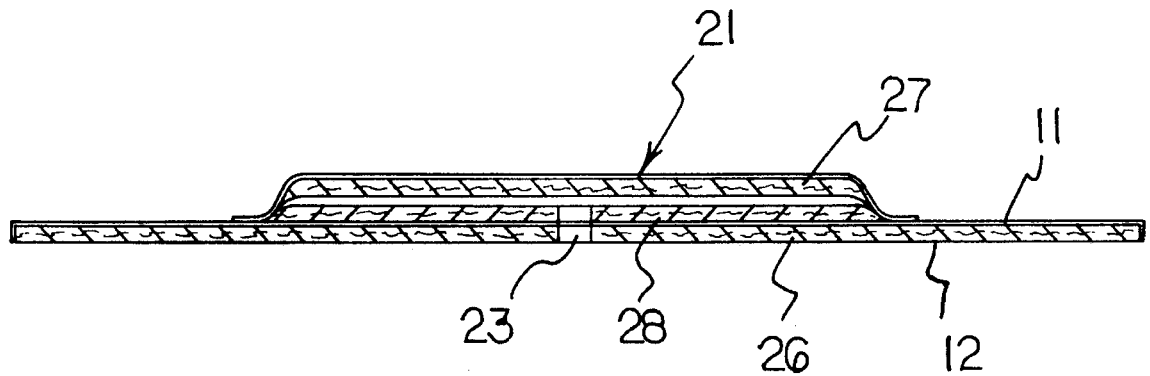
FIG. 5 is a cross-sectional view, taken along the lines 5—5 of FIG. 2 as indicated.

The male incontinence pants 10 of the invention comprises a single flexible web having an outer surface 11 formed of a fluid impermeable material, as illustrated in FIG. 5. The flexible web is provided with an inner surface 12 of a coextensive fluid absorbent material, also as indicated in FIG. 5, indicated by the inner surface 12. The flexible web is provided with a first web 13 of a first width as defined between the first web first sides 14. The first web 13 is secured to a second web 15 having a second width less than the first width, as the second width is defined between the second sides 16. A connecting web portion 17 interconnects the first and second webs 13 and 15 connecting the forward and rear respective ends of the respective first and second webs. The connecting web portion is of a third width less than the second width and extends between the opposed facing edges of the respective first and second webs, such that respective spaced key-hole shaped openings 18 extend between the first and second webs and extend into the connecting web 17 from the sides of the first and second webs, such that each of the key-hole shaped openings 18 includes a semi-circular portion adjacent the connecting web portion on opposed sides thereof, with each semi-circular portion extending to opposed facing linear edges of the first and second webs, such that the first and second linear web edges, such as indicated in the FIG. 4, provide for a linear seaming of the first and second webs when secured together by the connecting tape members 22 that are secured to the first web sides 14 of the first web 13. The semi-circular portions comfortably accommodate the individual's legs therethrough, such as indicated in the FIGS. 3 and 4.

Figure 1:
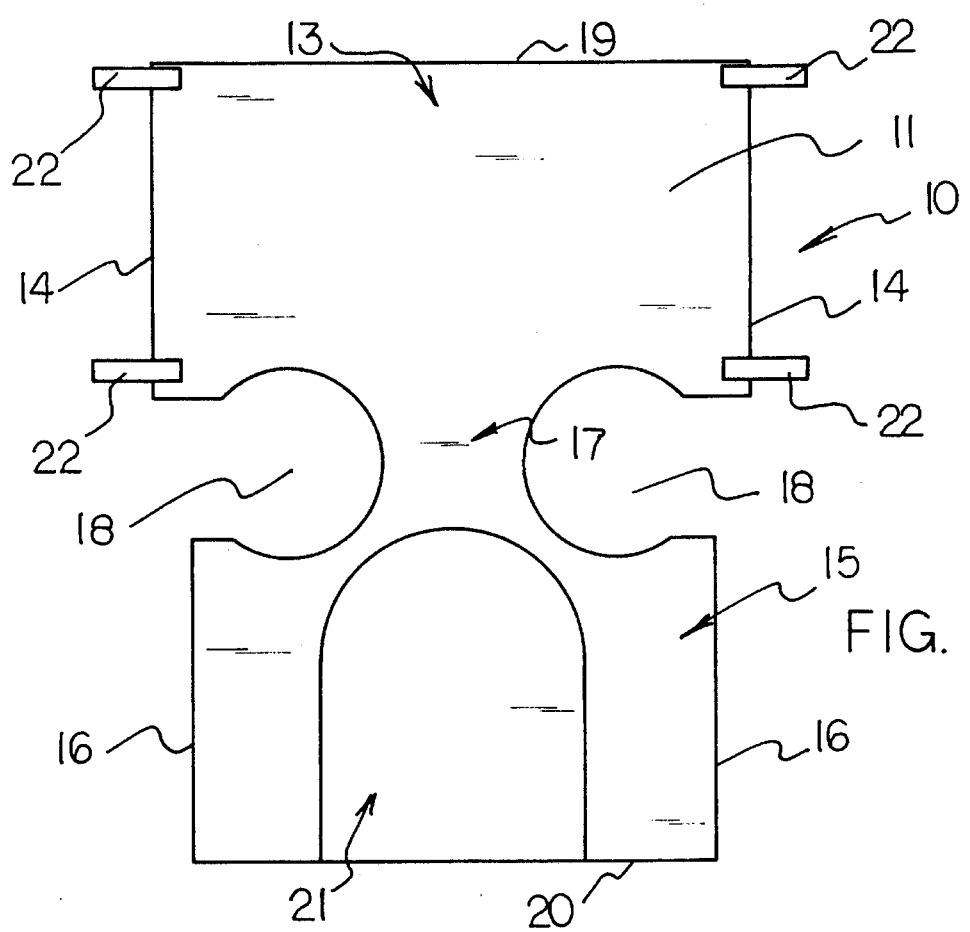
FIG. 1 is a top plan view of the pants construction.
Figure 2:
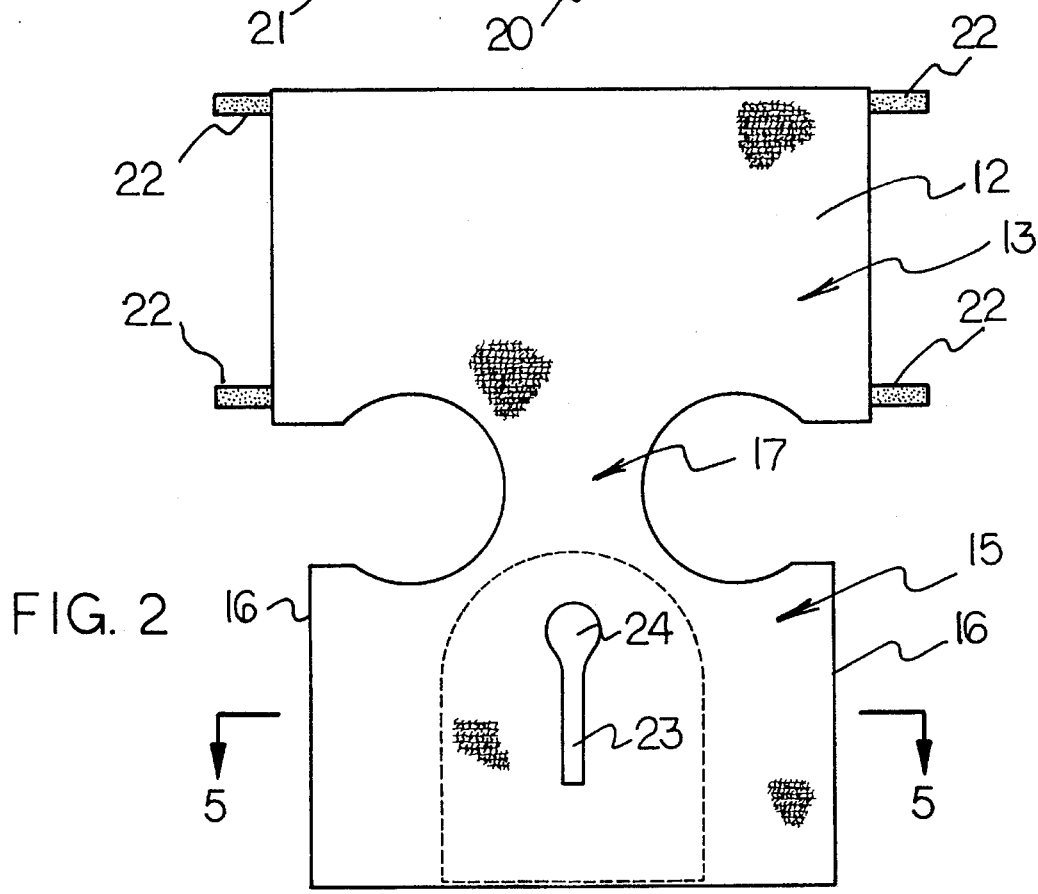
FIG. 2 is a bottom plan view of the pants construction.

As indicated, the first web 13 is provided with a first web rear edge 19 and the second web 15 having a second web forward edge 20, such that a pocket member 21 is fixedly secured to the outer surface 11 of the second web 15 and extends from the second web forward edge 20 to the connecting web 17 and the pocket 21 is oriented substantially medially of the second web sides 16, as illustrated in the FIG. 1 and the FIG. 2.

Figure 6:
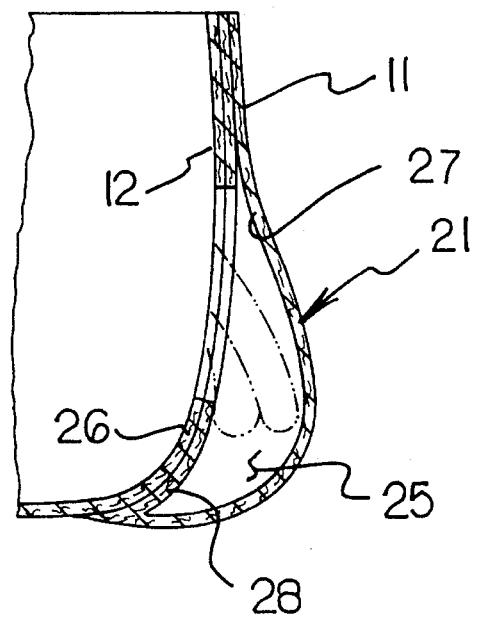
FIG. 6 is an enlarged, cross-sectional view, taken along the lines 6—6 of FIG. 3 as indicated.

Extending through the second web 15 from the inner surface 12 is an elongate entrance slot 24 oriented substantially medially of and parallel between the second web, sides 16, and with the slot extending to a lower semi-circular second end 24 spaced from the slot first end as oriented in adjacency to a second web forward edge 20, as the semi-circular opening 24 is oriented in adjacency to the connecting web 17, such as illustrated in FIG. 2. The slot 23 is arranged to accommodate the penile portion of an individual's anatomy, as the semi-circular second end 24 is arranged to accommodate the scrotum portion, in a manner as indicated in FIG. 6. Further it should be noted that the pocket cavity 25 is provided to provide for fluid absorbency and to this end (see FIGS. 5 and 6), the inner surface 12 includes the inner fluid absorbent layer 26, with a first pocket layer 27 contiguous with the pocket at the outer surface 11, with a second pocket fluid absorbent layer 28 coextensive with the first pocket layer 27 and oriented in adjacency to the inner fluid absorbent layer 26, wherein this triple layer construction provides for enhanced fluid absorbency as well as accumulation within the pocket cavity 25.

It is to be understood that while certain forms of the present invention have been illustrated and described herein, it is not to be limited to the specific forms or arrangement of parts described and shown.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may e resorted to, falling within the scope of the invention.

What is claimed and desired to be protected by Letters Patent of the United States is as follows:

1. Male incontinence pants, comprising, a flexible web, the flexible web having an outer surface spaced from an inner surface, the flexible web further comprising a first web spaced from a second web, the first web having a first web rear edge spaced from a first web forward edge, the second web having a second web rear edge spaced from a second web forward edge, and a connecting web, the connecting web interconnecting the first web forward edge and the second web rear edge, and a pocket member having a pocket cavity, and the pocket cavity extending from the second web, and extending from the second web forward end to the connecting web, and the pocket member oriented medially between the second web sides of the second web;

an entrance slot directed into the pocket cavity extending from the inner surface of the second web, and the slot having a first end adjacent to the second web forward end, and the pocket entrance slot having a semi-circular second end to accommodate a male scrotum, with the pocket entrance slot extending medially between the second web sides and oriented substantially orthogonally relative to the second web forward end.

2. Pants as set forth in claim 1 wherein at least one key-hole shaped opening is provided, with said one key-hole shaped opening oriented on each side of the connecting web, and the key-hole shaped opening is positioned between the first web and the second web, and said key-hole shaped opening includes a semi-circular portion positioned adjacent to the connecting web, and said key-hole shaped opening extends to opposed and facing linear edges, and the first web having first web first sides and at least one connecting member mounted to each of the first web sides for securement to the second web sides, wherein the linear edges of each key-hole shaped openings provide for linear alignment of the linear sides when the connecting members are secured to the second web.

3. Pants as set forth in claim 1 wherein the second web includes an inner fluid absorbent layer extending from the inner surface to the pocket cavity, and the pocket cavity having a first pocket layer coextensive with the outer surface and the pocket cavity, and a second pocket layer spaced from the first pocket layer coextensive with the first pocket layer and the cavity, and the second pocket layer of fluid absorbent material oriented adjacent to the inner fluid absorbent layer.

* * * * *